United States Patent [19]

Goldenberg

[11] Patent Number: 5,800,172
[45] Date of Patent: Sep. 1, 1998

[54] DENTAL TURBINE HAND PIECE WITH LIGHT AND ROTARY HEAD

[76] Inventor: Boris Goldenberg, 1305 E. 18th St., #5D, Brooklyn, N.Y. 11230

[21] Appl. No.: 909,258

[22] Filed: Aug. 11, 1997

[51] Int. Cl.[6] .................................................. A61C 1/05
[52] U.S. Cl. ........................................ 433/132; 433/29
[58] Field of Search ................................ 433/29, 132

[56] References Cited

U.S. PATENT DOCUMENTS

| | | | |
|---|---|---|---|
| 3,731,384 | 5/1973 | Brooks et al. | 433/132 |
| 4,153,993 | 5/1979 | Kataoka et al. | 433/132 |
| 4,303,393 | 12/1981 | Gentry | 433/132 |
| 4,568,642 | 2/1986 | DeForrest et al. | 433/132 |
| 4,642,738 | 2/1987 | Meller | 433/29 |

*Primary Examiner*—John J. Wilson
*Attorney, Agent, or Firm*—Ilya Zborovsky

[57] ABSTRACT

A dental turbine hand piece has a body, a turbine rotatable in the body about an axis, a light source arranged on the body, and means for current supply to the light source, a magnetic element formed on one of the turbine and the body, and a winding provided on the other of the turbine element in the body, so that during rotation of the turbine and in the body and interaction between the magnetic member and the winding and electric current is generated which is supplied to the light source.

6 Claims, 2 Drawing Sheets

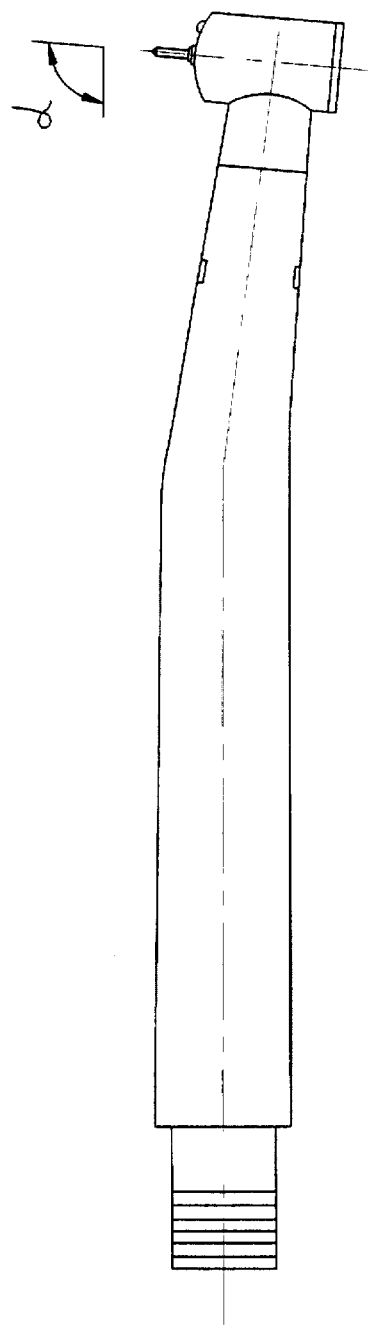
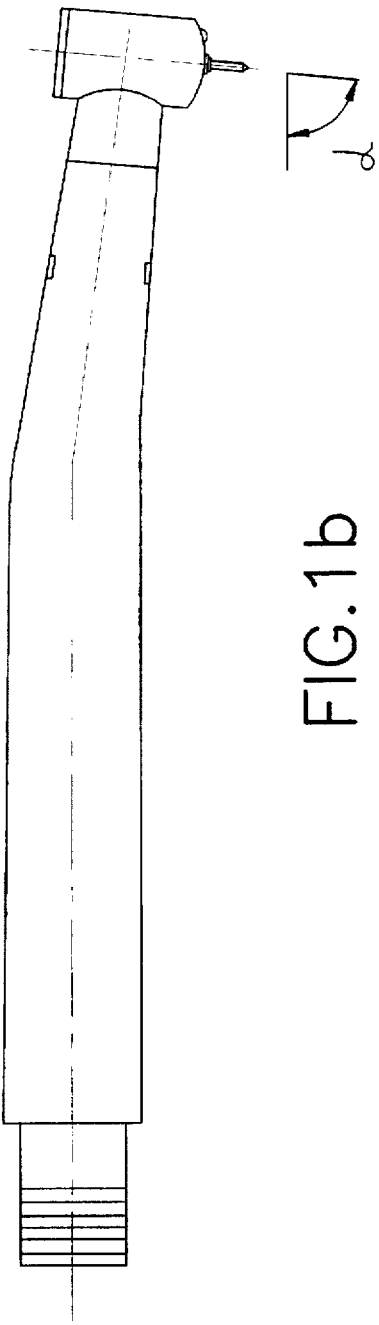
FIG.1a
FIG.1b

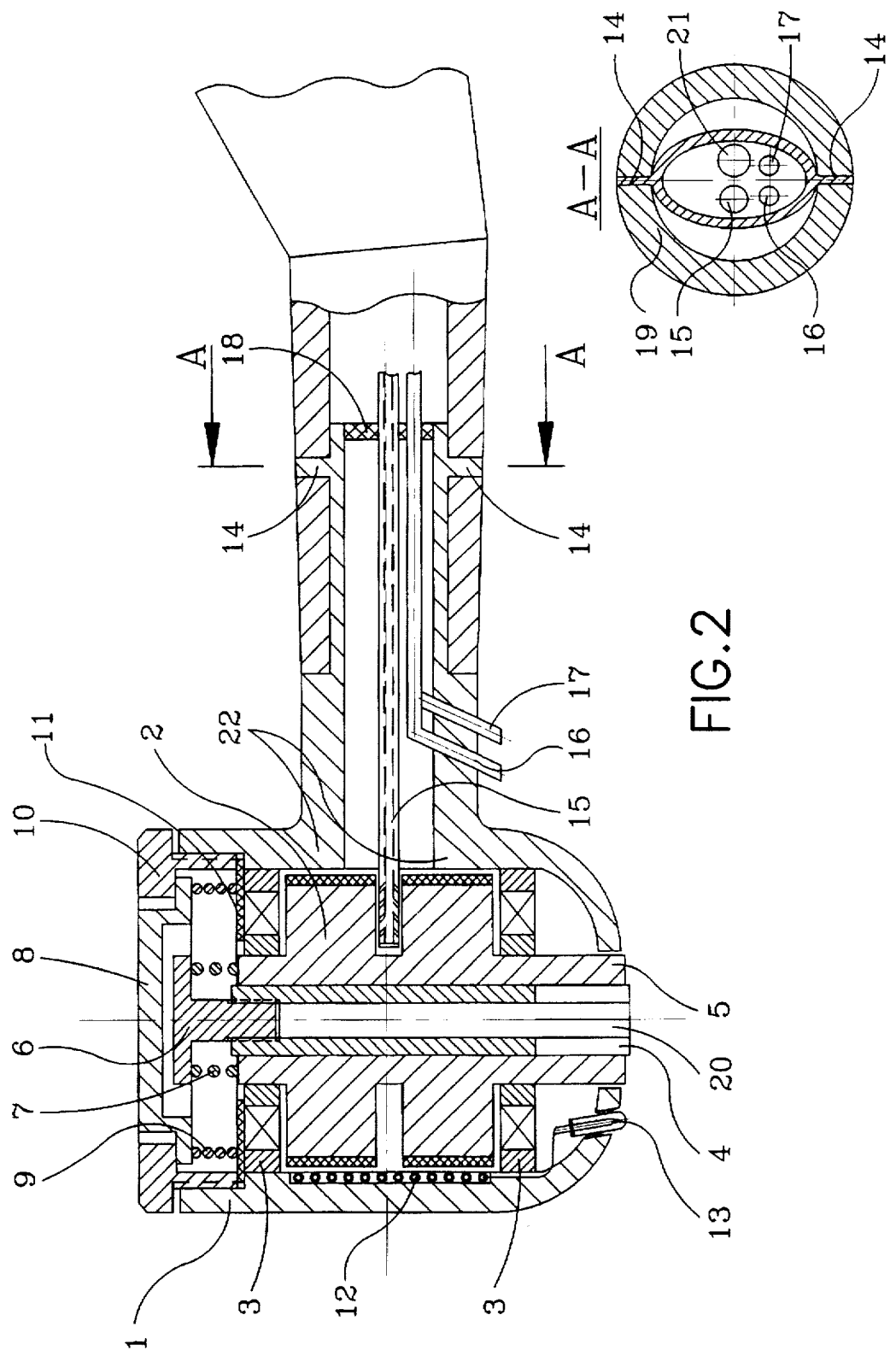

DENTAL TURBINE HAND PIECE WITH LIGHT AND ROTARY HEAD

BACKGROUND OF THE INVENTION

The present invention relates to a dental turbine hand piece with a light and rotary head.

Dental turbine hand pieces are well known and used in dentistry. Their heads are provided with light in order to improve the visibility during dental work. A source of light is usually a bulb mounted in a head of the hand piece which is supplied with electric current with 2-3 v. This construction however has the disadvantage that it is necessary to provide a separate current source and a special hose in which, in addition to an air light, also electrical conductors have to be incorporated. This is why it is not possible to replace a conventional turbine, with the turbine hand piece with a light, without additional adjustment of the dental devices. Also, a loss of contacts leads to an illumination loss during the dental work. Another disadvantage of the dental hand pieces is their shape which forms an obtuse angle between the drilling bit and the axis of the hand piece, which facilitates treatment of front teeth, but is complicated for treatment of molars in a neck-close zone from a distal side, since it requires expansion of a mouth cavity.

SUMMARY OF THE INVENTION

Accordingly, it is an object of the present invention to provide a dental turbine hand piece, which avoids the disadvantages of the prior art.

In keeping with these objects and with others which will become apparent hereinafter, one feature of present invention resides, briefly stated, in a dental turbine hand piece which has a turbine element connected to a drilling tool and rotatable by a fluid so as to rotate the drilling tool; means cooperating with said turbine element so that during the rotation of the turbine element electrical current is generated by the turbine element; and a light source supplied by the current produced during the rotation of the turbine element.

When the dental turbine hand piece is designed in accordance with present invention, it eliminates the disadvantages of the prior art. The light on the working end of the drilling tool is provided without a separate electrical current source, and a possibility of facilitation of treatment of molars in a near-neck area from a distal side is combined with the possibility of treatment of front teeth as well.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIGS. 1a and 1b are views showing a dental turbine hand piece in two positions with an obtuse angle between a turbine axis and a drilling tool, and during turning of the head of the turbine by 180° so that an acute angle is formed between the turbine axis and a drilling tool of the inventive dental turbine hand piece;

FIG. 2 is a view showing a section of a head of the turbine of the inventive hand piece which is connected with a body of the hand piece; and FIG. 3 is a view showing a section taken along the line III—III in FIG. 2.

DESCRIPTION OF PREFERRED EMBODIMENTS

A dental turbine hand piece has a head with a body identified with reference numeral 1. A double turbine 2 is rotatably supported in the head. Its vanes are provided with a magnetic element on their outer ends. The turbine is rotated in a rotary bearing stream and provided with a chuck for a drilling tool, such as drilling bit. The chuck is arranged in an axle 5 and provided with an abutment 6 and a spring 7. A button 8 is provided for opening of the chuck and has a button spring 9. The device further has a stop knot 10 with a washer 11. The hand piece also has a stator provided with a winding 12.

The hand piece further has a light source which is formed for example as a micro bulb. Stop projections 14 are provided for the turbine head. A pipe 15 supplies air for the turbine head, a pipe 16 supplies cooling water to the drilling tool, a pipe 17 supplies a cooling air to the drilling tool. The insert 18 supports the above mentioned pipes. Reference numeral 19 identifies a body of the turbine and reference numeral 20 identifies an opening for the drilling tool.

The dental turbine hand piece in accordance with the present invention operates in the following manner.

When the button 8 is pressed, it presses against the stop 6 of the chuck and moves outwardly the chuck 4 from the axle of the turbine so as to increase the opening 20 for insertion of the drilling tool. When the pressure from the button 8 is removed, the chuck under the action of the spring 7 resumes its initial position and clamps the drilling tool. The button 8 is returned by the spring 9 to its initial position and no longer interferes with the rotation of the turbine. Air under pressure is supplied in the pipe 15 to the vanes of the turbine 2 and rotates the turbine together with the drilling tool. In order to increase the power of the turbine 2, it is formed as a double turbine. The pipe 15 which supplies air has one end located between the two turbine parts so that air is supplied to the turbine through a series of openings arranged at an angle to the pipe, so that a vector of exiting air is almost perpendicular to the turbine vanes. The other end of the pipe is held by the insert 8. The pipe supplying the air is connected with an outer system of air supply through a flexible hose, which can be wound-on and wound-out inside the turbine body by one half revolution. The withdrawal of the waiste air is performed through passages 22 and the pipe 21 as shown in FIG. 3.

When the turbine 2 rotates, electrical current is generated in the winding 12 of the stator and supplied to the light source or bulb 13. Thereby no additional current supply is needed.

The turbine head is introduced into the body 19 of the turbine hand piece and fixed by two projections which are formed of one piece with the end part of the turbine head. When a pressure is applied to the projections, they disengage from the turbine head and therefore the turbine head can be turned by 180°. Then, the projections again engage with the turbine body. In order to impart elastic properties to the engaging system, the end part of the head is formed as an ellipse as shown in FIG. 3.

It will be understood that each of the elements described above, or two or more together, may also find a useful application in other types of constructions differing from the types described above.

While the invention has been illustrated and described as embodied in a dental turbine hand piece with light and rotary head, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed and desired to be protected by Letters Patent is set forth in the appended claims:

1. A dental turbine hand piece, comprising a body; a turbine rotatable in said body about an axis; a light source arranged on said body; and means for current supply to said light source, said means including a magnetic element formed on one of said turbine and said body, and a winding provided on the other of said turbine and said body, so that during rotation of said turbine element in said body and interaction between said magnetic member and said winding and electric current is generated which is supplied to said light source.

2. A dental turbine hand piece as defined in claim 1, wherein said magnetic member is formed on vanes of said turbine element, while said winding is located on said body.

3. A dental turbine hand piece as defined in claim 1, wherein said turbine has a turbine head which is movable and turnable about an axis of its rear portion by 180°.

4. A dental turbine hand piece as defined in claim 3, wherein said turbine has a turbine body, said turbine head is mountable with said turbine body by projections so that when said projections are disengaged said turbine head is turnable, and then said projections are automatically engaged to fix a position of said turbine head.

5. A dental turbine hand piece as defined in claim 1, wherein said turbine is formed as a double turbine having two turbine parts.

6. A dental turbine hand piece as defined in claim 5; and further comprising means for supplying air directly to vanes to increase a power of said turbine.

* * * * *